United States Patent [19]

Kovács et al.

[11] Patent Number: 4,462,993
[45] Date of Patent: Jul. 31, 1984

[54] AMINOACRIDINE-α, β-(D)- OR -(L)-N-GLYCOSIDE DERIVATIVES, THE SALTS THEREOF AND A PROCESS FOR THE PREPARATION OF SUCH COMPOUNDS

[75] Inventors: Antal Kovács; András Lipták; Pál Nánási; Jóránt Jánossy; István Csernus; János Erdei; István Kaszab; Kálmán Pólya, all of Debrecen; András Neszmélyi, Budapest, all of Hungary

[73] Assignee: Biogal Gyogyszergyar, Debrecen, Hungary

[21] Appl. No.: 353,388

[22] Filed: Mar. 1, 1982

[30] Foreign Application Priority Data

Feb. 27, 1981 [HU] Hungary .................................. 474/81

[51] Int. Cl.³ ........................ A61K 31/70; C07H 17/00
[52] U.S. Cl. ...................................... 424/180; 536/23; 536/55
[58] Field of Search ...................... 536/55, 23; 424/180

[56] References Cited

U.S. PATENT DOCUMENTS 4,314,061  2/1982  Murdock et al. .................... 546/104
4,335,244  6/1982  Kaplan et al. ........................ 546/106

OTHER PUBLICATIONS

Studies of Optical Properties of Acridine Orange--Glucose Sulfate Complex, by K. Nishida, Y. Ando and H. Nomura.
Letter to the Editors, Wisenschaftliche Kurzberichte.
Chemical Abstracts 89:112282n (1978).
Chemical Abstracts 91:142065c (1979).
Chemical Abstracts 88:62551f (1978).
Chemical Abstracts 86:5791w (1977).
Chemical Abstracts 91:65609d (1979).

*Primary Examiner*—Ethel G. Love
*Attorney, Agent, or Firm*—Karl F. Ross; Herbert Dubno

[57] ABSTRACT

The invention relates to novel aminoacridine-α,β-(D)- and -(L)-N-glycoside derivatives, the salts thereof and to a novel process for the preparation of such compounds and salts. The novel compounds have the formula I

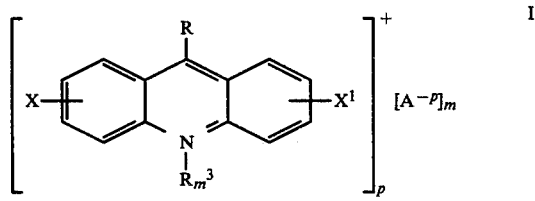

wherein R is hydrogen or a group of the formula II

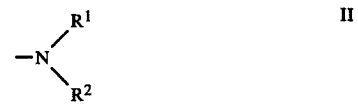

wherein n=0 or 1, p=1 or 2, $A^{-p}$ is an anion, preferably halogenide,
  $R^1$ is hydrogen or a methyl group and
  $R^2$ is hydrogen or a sugar residue, or R is dimethylamine,
and the two substituents
  X and $X^1$ are identical or different and stand for hydrogen, a group of the formula II, dimethylamine, halogen, a $C_{1-4}$ alkyl group, a $C_{1-4}$ alkoxy group, for a nitro-, cyano-, carbomethoxy-, carbamoyl-, phenyl- or a $C_{1-4}$ alkylphenyl group,
with the restriction that at least one of the substituents R, X and $X^1$ represents a group of formula II with $R^2$=sugar residue, and
  $R^3$ is hydrogen or a $C_{1-5}$ alkyl group.

25 Claims, No Drawings

AMINOACRIDINE-α, β-(D)- OR -(L)-N-GLYCOSIDE DERIVATIVES, THE SALTS THEREOF AND A PROCESS FOR THE PREPARATION OF SUCH COMPOUNDS

The invention relates to novel aminoacridine-α,β-(D)- or -(L)-N-glycoside derivatives, the salts thereof and a chemically unique process for the preparation of such compounds and salts. The novel compounds correspond to the formula I $$\left[\begin{array}{c}\text{acridine structure with R at 9, X at 6, X' at 3, N-R}_n^3\end{array}\right]_p^+ [A^{-p}]_n \quad \text{I}$$

wherein
n=0 or 1,
p=1 or 2, $A^{-p}$ is an anion, preferably halogenide,
R is hydrogen or, a group of the formula II $$-N\begin{array}{c}R^1\\R^2\end{array} \quad \text{II}$$

wherein
$R^1$ is hydrogen or a methyl group and
$R^2$ is hydrogen or a sugar residue,
or R is dimethylamino,
and the two substitutents
X and X' are identical or different and stand for hydrogen, a group of the formula II dimethylamino, halogen, a $C_{1-4}$ alkyl group, a $C_{1-4}$ alkoxy group, for a nitro-, cyano-, carbomethoxy-, carbamoyl-, phenyl- or a $C_{1-4}$ alkyl phenyl group, and
$R^3$ is hydrogen or a $C_{1-5}$ alkyl group, with the restriction that at least one of the substituents R, X and X' represents a group of the formula $-NR^1R^2$ wherein $R^2$ is a sugar residue.

The possible sugar residues in group II are as follows: D-glucosyl-, D-galactosyl-, D-mannosyl-, D-xylosyl-, D- and L-arabinosyl-, D-ribosyl-, 6-desoxy-D-glucosyl-, 6-desoxy-D-galactosyl-, L-rhamnosyl-, 2-desoxy-D-arabinosyl-, 2-acetoamido-2-desoxy-D-glucosyl-, daunosaminyl-, maltosyl-, cellobiosyl-, lactosyl-, gentiobiosyl- or laminaribiosylgroup.

From literature it is known that the aminoacridines are the most important and most interesting acridine derivatives. The attention paid to the aminoacridines cannot only be attributed to the fact that they possess a broader spectrum of physical and chemical properties than any other acridine group but also to the fact that most of the acridine medicaments and -colorants belong to this group (A. Albert, The Acridines, 2nd Edition, Arnold, London; Acheson, R. M. (ed.) (1973), ACRIDINES 2nd Edn., J. Wiley and Sons Inc. New York; A, Albert: Selective Toxicity, 5th Edn., Chapman and Hall, London, 1973; A. Nasim and T. Brychy: Genetic Effects of Acridine Compounds, Mutation Research 65, 261–288 (1979); Quinacridine and Other Acridines in Antibiotics Vol. III, 203–233, Springer-Verlag, Berlin).

The two aminoacridines proflavine (3,6-diaminoacridine) and acriflavine (3,6-diamino-10-methyl-acridine, 10-methylproflavine) are e.g. known which exert a certain antimicrobial effect.

From the British patent specification No. 1,093,847 the 1-nitro-9-dialkylaminoalkyl-acridines are known. They are prepared by condensing the 1-nitro-9-chloroacridine with the corresponding dialkylaminoalkylamine. From the British patent specification No. 1,528,723 and the U.S. Pat. No. 4,150,231, aminoacridines substituted in position 9 and exerting a pharmacological effect are known, too.

The compounds known from these literature sources are toxic and unstable, in an aqueous medium they decompose to the biologically inactive 1-nitroacridone. Furthermore it is disadvantageous that the solutions of the compounds have a pH-value of about 4 what can lead to inflammation at the locus of injection when they are administered as injection. The compounds show also a negative effect on the digestive tract, they cause e.g. nauses and vomitus.

It was the aim of the invention to find pharmacologically efficacious aminoacridines the properties of which are more advantageous. Surprisingly it has been found that the novel aminoacridine-glycosides of the formula I possess valuable pharmacological properties and that by the incorporation of the sugar group into the molecule their properties completely differ from those of the starting substances.

Numerous processes are known for the preparation of N-glycosides from the literature. However, it appeared that none of the known processes was suitable for the preparation of compounds of the formula I. According to the melting method of WEYGAND (F. Weygand: Chem. Ber. 72, 1663 (1939); 73, 1239 (1940) as well as to the KOENIGS-KNORR-raction (W. Koenigs, E. Knorr: Chem. Ber. 34, 957 (1901) the compounds could not be obtained at all. When applying the method of PIGMAN (L. Rosen, J. W. Woods, W. Pigman: J. Org. Chem. 22, 1727 (1957) the reaction took place extremely slowly, and the other processes known from the literature (e.g. R. Kuhn, Chem. Ber. 68, 1765 (1935); 69, 1745 (1940); R. Bognár, P. Nánási: Nature 171, 475 (1953); M. Frerejacque, Compt. Rend. 202, 1190 (1936) provide reaction mixtures with undesired by-products whereby the isolation of the glycoside was rendered more difficult and the yields were considerably lowered.

According to the invention the aminoacridine-α,β-(D)- or -(L)-N-glycoside derivatives of the formula I wherein R, $R^3$ and X are as defined above are prepared by reacting a compound of the formula III, $$\left[\begin{array}{c}\text{acridine structure with Z at 9, Y at 6, Y' at 3, N}_+\text{-R}_n^3\end{array}\right]_p [A^{-p}]_n$$

wherein
Z is an amino-, methylamino- or dimethylamino group or hydrogen,
$R^3$ is as defined above, and the two substituents
Y and Y' are identical or different and stand for hydrogen, an amino-, methylamino- or dimethylamino group or for halogen, a $C_{1-4}$ alkyl or alkoxy group, a nitro-, cyno, carbomethoxy-, carbamoyl-, phenyl- or $C_{1-4}$ alkylphenyl group, with the proviso that at least one of the substituents Z, Y and Y represents a free or monosubstituted amino group, or the acid addition salts thereof with hexoses, pentoses, desoxy-, desoxyamino-, N-acetyl-hexoses, -pentoses and/or N-methylated aminosugars, isolating the reaction product, optionally acetylating the sugar residue, optionally separating the mono-, di- and triglycosides from each other, optionally reacting the monoglycosides to di- or triglycosides in the described way and optionally forming salts from the obtained compounds of the formula I.

It is surprising that the compounds of the formula I can be prepared in the way described above with a yield of about 90% since the known processes for the preparation of glycoside were unsuccessful. Therefore the disclosed process which is simple and economical and which has not been used for the preparation of N-glycosides up to now must be considered as novel and chemically unique. Furthermore it is surprising that different sugar residues can be simultaneously incorporated into the acridine molecule with the process according to the invention.

It is suitable to carry out the reaction in the presence of an acidic catalyst. As acidic catalyst e.g. hydrochloric acid is suitable. Generally the reaction is carried out at a temperature of 20°-95° C. As reaction medium acetone containing water proved to be especially suitable.

The reaction products are separated and purified in a way known per se. For purification the products are washed, optionally recrystallized or submitted to column chromatography, too. For chromatography silica gel is preferably used and the elution takes place with a mixture of acetone and ammonia.

The incorporation of the sugar group into the aminoacridine molecule modifies its properties in an unforeseen way. Thus e.g. 3,6-diamino-acridine and 3,6-diamino-10-methyl-acridine are efficacious in concentrations of 50 µg/ml against microorganisme (*Bacillus subtilis, Salmonalla typhy-murium, Proteus vulgaris, Escherichia coli, Shigella flexneri* etc.) while the diglucoside of the 3,6-diamino-acridine is inefficacious also in concentrations of 500 µg/ml against the named microorganisms. Inversely the aminoacridines are inefficacious against fungi while the diglucoside of 3,6-diamino-10-methyl-acridine is efficacious e.g. against Aspergillus funigatus and Aspergillus niger.

As it is known from the literature the growth of the Ehrlich ascites tumor is inhibited by 3,6-diamino-10-methylacridine (Schümelfelder et al., Z. Krebsforsch, 63, 129 (1959)). The diglucoside of this compound not only inhibits the development of the Ehrlich tumor but also prevents its formation (test animals: mice and rats) and besides differs from the starting compound positively in so far as in a corresponding dose (6.25 mg/kg–12.5 mg/kg i.p.) the diglucoside improves the state of the animal concerning its condition, too, i.e. it suppresses the cancer.

By the incorporation of one or more sugar residue(s) the toxicity of the compounds is influenced positively, too. The results of toxicity measurements carried out at CFLP-mice (female) (Litchfield, J. T. and Wilcoxon F.: J. Pharmacol. 96, 99 (1949) are summarized in the following Table.

|  | $LD_{50}$ (mg/kg) | |
| --- | --- | --- |
|  | i.p. | i.v. |
| 3,6-diamino-acridine | 84 | 65 |
| 3,6-diamino-acridine-diglucoside | 280 | 87 |
| 3,6-diamino-10-methyl-acridine | 60 | 14 |
| 3,6-diamino-10-methyl-acridine-diglucoside | 210 | 37 |

Finally, for the literature it is known that the acridine compounds acriflavine and proflavine were used during World War II for the disinfecting of wounds (Hawking, F.: Lancet 1, 710 (1943); Ungar J. and Robinson, F. A.: J. Pharmacol. Exp. Ther. 80, 217 (1944); Albert A.: The Acridines, 2nd Edn., Arnold, London (1966). As it turned out, however, the compounds slowed down the healing of the wound and caused tissue necrosis, too. The diglucosides of the mentioned compounds, however, did not cause (tests with female CFY-rats) any organellum-specific tissue modifications. The compounds were adminstered i.p. In the tissues of the offsprings of the treated rats any organellum-specific change could be detected neither macroscopically nor microscopically. From this fact it can be concluded that the compounds do not exert any teratogenic activity.

From the literature it is also known that the compounds proflavine and acriflavine can cause mutation of certain objects. With the help of the test of P. Mollet and I. Szabad (Mutation Research 51, 293–296 (1978) on Drosophila melanogaster it could be stated that the glycosides of the invention do not exert any mutagenic activity.

As it appears from the above statements, the acridine-N-glycosides of the invention are free of unpleasant properties which are characteristic of the starting substances containing no sugar residues. Due to their antitumor effect the compounds according to the invention can be used as therapeutica against tumor diseases.

A test with the Ehrlich-carcinoma was carried out with 50 mice each as test group and as K control group. The animals were intraperitoneally infected with $5 \times 10^6$ cells each of the ascites tumor according to Ehrlich. On the first, second and third day after the infection half of the mice were treated with 12.5 mg/kg.d of 10-methyl-proflavine-diglucoside. The results are summarized in the following table.

|  | Change of body weight in g on the | | | Average surviving time (d) |
| --- | --- | --- | --- | --- |
|  | 7th | 12th | 21st day |  |
| Control | +8.1 | +19.0 | — | 13.2 |
| Treated | +1.2 | +2.0 | +2.6 | 40.0[1] |

[1]On the 40th day all treated animals were still living, the observation was stopped.

The invention is further illustrated in the following Examples.

Example 1

3,6-Di-(β-Di-glucopyranosyl-amino)-acridine

In a round-bottom flask with a volume of 3 l provided with a reflux condenser and a mixer 66.0 g (0.33 mole) of D-glucose-monohydrate and 36.9 g (0.15 mole) of 3,6-diamino-scridine-hydrochloride are suspended in a mixture of 1350 ml acetone and 150 ml of water under heavy stirring. The suspension is heated to a temperature of 45° C. and then reacted with 10 ml of concentrated hydrochloric acid. After about 5 minutes of stirring the solution becomes clear, after further 2-3 minutes the product begins to precipitate. The reaction mixture is placed into an ice water bath for an hour, then the precipitate is isolated. The precipitate is dissolved in 250 ml of water and the solution is admixed with 2 l of acetone. The flocculent precipitate is isolated, it is washed with 200 ml of ethyl-acetate at first, then with 100 ml of ether and finally it is dried in vacuo. This reprecipitation is repeated twice. 70.0 g (87.5%) of the product are obtained. Melting point: 190°–195° C.; $[\delta]_D = -145.8°$ (c=0.75, dimethylformamide).

TLC: Silica gel 60 F254 (DC-aluminium roll, art. 5562, Merck); running agent: acetone and ammonium hydroxide in a ratio of 65:35—$R_f = 0.41$ Analysis for $C_{25}H_{31}O_{10}N_3$ (M=533.27) Calculated: C 56.26%; H 5.86%; N 7.88%. Found: C 55.42%; H 5.69%; N 8.01%.

Example 2

3-Amino-6-$\beta$-D-glucopyranosyl-amino-acridine

The liquid phase isolated from precipitate according to Example 1 contains besides unreacted starting substance and little diglucoside also the monoglucoside. The solution is evaporated in vacuo. From the obtained 15 g of evaporation residue 3 g are applied onto a column with a diameter of 7 cm and a height of 25 cm which is filled with 300 g of silica gel G and they are eluted with a mixture of acetone and ammonium hydroxide in a ratio of 65:35. Fractions of 10 ml each are collected the composition of which is controlled by thin layer chromatography. For this the same solvent mixture is used as for the column chromatography. The fractions containing the monoglucoside are united and evaporated in vacuo. The residue is processed with 50 ml of ethylacetate and then filtered.

Yield: 1.25 g; melting point: 190° C.; $[\alpha]_D = -95.3°$ (c=0.55, dimethylformamide).

TLC: Silica gel 60 F254 (DC-aluminium roll, art. 5562, Merck), running agent: acetone and ammonium hydroxide in ratio of 65:35—$R_f = 0.79$.

Analysis for $C_{19}H_{21}O_5N_3$ (M=371.19) Calculated: C 61.42%; H 5.70%; N 11.32%. Found: C 60.95%; H 5.60%; N 15.05%.

EXAMPLE 3

3,6-Di-($\beta$-D-galactopyranosyl-amino)-acridine

In a round-bottom flask with a volume of 3 l provided with a reflux condenser and a mixer 60.0 g (0.33 mole) of D-galactose and 36.9 g (0.15 mole) of 3,6-diaminoacridine-hydrochloride are suspended in a mixture of 1350 ml of ethanol and 150 ml of water under heavy stirring. The suspension is heated to 70° C. under stirring and reacted with 7.5 ml of concentrated hydrochloric acid. The solution rendered slowly cloudy by a flocculent precipitate is stirred at the given temperature for another 2 hours and then put into a refrigerator (+4° C.) for 16 hours. The liquid phase is isolated and the residue is dissolved in 150 ml of water. The solution is run under continuous stirring into 3 l of ethanol containing 5% of water. The flocculent precipitate is filtered off and dried. The reprecipitation is repeated twice in the described manner.

Yield: 60.5 g (75.6%), melting point: 200° C., $[\alpha]_D = -25.4°$ (c=0.31, dimethylformamide).

TCL: Silica gel 60 F 254 (DC-aluminium roll, art. 5562, Merck), running agent: acetone and ammonium hydroxide in a ratio of 7:3—$R_f = 0.33$.

Analysis for $C_{25}H_{31}O_{10}N_3$ (M=533.27) Calculated: C 56.26%; H 5.86%; N 7.88%. Found: C 55.49%; H 5.69%; N 7.96%.

Example 4

3,6-Di-(2', 3', 4', 6'-tetra-O-acetyl-$\alpha$-D-galacto-pyranosyl-amino)-acridine (supplementary acetylation)

60.0 g of 3,6-Di-($\alpha$-Dgalactopyranosyl-amino)-acridine obtained according to Example 3 are suspended in a mixture of 600 ml of pyridine and 600 ml of acetic acid anhydride. The reaction mixture is stirred at room temperature for 18 hours and then evaporated in vacuo (12 Torr) to a volume of 150 ml. This residue is poured into 600 g of icy water. The liquid phase is poured off the powdery precipitate which settles down well, but is badly filte rable. The precipitate is dissolved 1 l of dichloromethane. The solution is shaken out three times with 150 ml of water each, dried over sodium sulfate and then evaporated in vacuo. The evaporation residue is dissolved under heating and reflux in 200 ml of ethanol. On cooling to room temperature 8.0 g (8.2%) of the substance are separated in the form of long, needle-like crystals. These crystals are recrystallized twice from ethanol. Melting point: 225° C.; $[\alpha]_D = +73.6°$ (c=1.25, chloroform);

TLC: Silica gel 60 $F_{254}$ (DC-aluminium roll, art. 5562, Merck), running agent: dichloromethane and acetone in a ratio of 7:3—$R_f = 0.62$.

Analysis for $C_{41}H_{47}O_{18}N_3$ (M=869.51): Calculated: C 56.66%; H 5.45%; N 4.83%. Found: C 55.92%; H 5.36%; N 4.96%.

Example 15

3,6-Di-(2', 3', 4', 6'-tetra-O-acetyl-$\beta$-D-galacto-pyranosyl-amino)-acridine The mother liquor from which the product was crystallized for the first time according to Example 4 is evaporated to a volume of 75 ml. The solution is put into a refrigerator. After 8 hours of standing small, needle-like crystals are separated. They are filtered off and dried. 35.0 g (35.8%) of product are obtained. Melting point: 195° C., $[\alpha]_D = -20.3°$ (c=1.48, chloroform)

TLC: Silica gel 60 F254 (DC-aluminium roll, art. 5562 Merck), running agent: dichloromethan and acetone in a ratio of 7:3—$R_f = 0.56$.

Analysis for $C_{41}H_{47}O_{18}N_3$ (M=869.51): Calculated: C 56.66%; H 5.45%; N 4.83%. Found: C 56.08%; H 5.29%; N 4.68%.

EXAMPLE 6

3,6-Di-($\alpha$-L-rhamnopyranosyl-amino)-acridine 2.46 g ($10^{-2}$ mole) of 3,6-diamino-acridine-hydrochloride and 4.0 g ($2.2 \times 10^{-2}$ mole) of L-rhamnose-monohydrate are suspended in a mixture of 10 ml of water and 90 ml of ethanol. The reaction mixture is stirred intensively and heated to a temperature of 70° C. After the addition of 0.5 ml or concentrated hydrochloric acid the mixture is stirred at the given temperature for another 90 minutes, while shining, flocculent crystals separate. The mixture is left to stand at room temperature for 12 hours and then it is filtered. 3.6 g (71.8%) of product are obtained. It is dissolved in the solution of 0.5 ml of concentrated hydrochloric acid in 120 ml of water and the solution is added drop by drop to 240 ml of ethanol. The separated precipitate is filtered off and dried.

Melting point: 185° C., $[\alpha]_D = +145°$ (c=1.25, dimethylformamide);

TLC: Silica gel 60 F 254 (DC-aluminium roll, art. 5562, Merck), running agent: acetone and ammonium hydroxide in a ratio of 85:15—$R_f=0.21$.

Analysis for $C_{25}H_{31}O_8N_3$ (M=501.27) Calculated: C 59.93%; H 6.23%; N 8.39%. Found: C 60.19%; H 6.35%; N 8.26%.

EXAMPLE 7

3,6-Di-(α-D-ribopyranosyl-amino)-acridine

Under stirring 2.46 g ($10^{-2}$ mole) of 3,6-diamino-acridine-hydrochloride and 3.3 g ($2.2 \times 10^{-2}$ mole) of D-ribose are suspended in a mixture of 90 ml acetone and 10 ml of water. 0.5 ml of concentrated hydrochloric acid are added to the suspension heated to 45° C. After 2-3 minutes a clear solution is formed and after further 4-5 minutes the precipitate begins to separate. 25 minutes after the addition of the acid and liquid phase is separated, the precipitate is dissolved in 20 ml of water and the solution is poured into 200 ml of acetone. This reprecipitation is repeated twice. The product is filtered and dried. Yield: 2.5 g (52.8%), melting point: 180°-190° C., $[\alpha]_D = +141°$ (c=1.20, dimethylformamide);

TLC: Silica gel 60 F254 (DC-aluminium roll, art. 5562, Merck), running agent: acetone and ammonium hydroxide in a ratio of 75:25—$R_f=0.43$.

Analysis for $C_{23}H_{27}O_8N_3$ (M=473.24). Calculated: C 58.32%; H 5.75%; N 8.88%. Found: C 57.90%; H 5.89%; N 8.56%.

EXAMPLE 8

3,6-Di-(β-lactopyranosyl-amino)-acridine

Under continuous stirring 2.46 g ($10^{-2}$ mole) of 3,6-diamino-acridine and 7.92 g ($2.2 \times 10^{-2}$ mole) of lactose-monohydrate are suspended in a mixture of 80 ml of ethanol and 20 ml of water. The reaction mixture heated to 70° C. is reacted with 1 ml of concentrated hydrochloric acid and stirred at 70° C. for 3 hours. Then another 3.96 g ($1.1 \times 10^{-2}$ mole) of lactose are added and the mixture is stirred at the given temperature for another 4 hours. Then the mixture is left to stand at room temperature for 10 hours, the liquid phase is decanted and the precipitate is dissolved in 115 ml of water. The solution is added drop by drop to 1150 ml of ethanol. This reprecipitation is repeated three times. The product is filtered off and dried.

Yield: 6.1 g (70.8%), melting point: 210° C., $[\alpha]_D = -112.7°$ (c=0.52, dimethylformamide).

TLC: Silica gel 60 F254 (DC-aluminium roll, art. 5562, Merck), running agent: acetone and ammonium hydroxide in a ratio of 1:1—$R_f=0.35$.

Analysis for $C_{37}H_{51}O_{20}N_3$ (M=857.82); Calculated: C 51.81%; H 5.99%; N 4.90%. Found: C 50.61%; H 6.32%; N 4.61%.

EXAMPLE 9

3-(β-D-Glucopyranosyl-amino)-6-(α-L-rhamnopyranosyl-amino)-acridine 14.76 g (0.06 mole) of 3,6-diamino-acridine-hydrochloride, 12.00 g (0.06 mole) of D-glucose-monohydrate and 10.92 g (0.06 mole) of L-rhamnose-monohydrate are suspended in a mixture of 552 ml of acetone and 48 ml of water under stirring. The reaction mixture is heated to 45° C. and reacted with 4.0 ml of concentrated hydrochloric acid. After 5-6 minutes the solution is clear and after another 4-5 minutes an oily product begins to separate. 45 minutes after the acid addition the mixture is cooled to room temperature and then it is separated into the phases. The oily part containing solid substance, too, is washed twice with 50 ml of acetone each, then it is dissolved in 170 ml of water and the solution is dropped to a mixture of acetone and ethanol (1700 ml) in a ratio of 1:1. the orange-coloured precipitate is filtered off, washed with ethylacetate, then with ether and finally dried in vacuo. Weight: 18 g.

For further purification the substance is dissolved in 120 ml of distilled water and the solution is poured into 1200 ml of a mixture of acetone and ethanol in a ratio of 2:1. 14.5 g of precipitate are obtained which are washed and dried in the described manner. The reprecipitation is repeated three times.

300 g of Merck-silica gel 40 (70-230 mesh, 0.063-0.2 mm) are suspended in 600 ml of a mixture of acetone, ammonium hydroxide and water prepared in a ratio of 70:15:15. The suspension is filled into a column and while the solution is flowing off, the silica gel is settling down in the column, 1.5 g of the raw product are added to 60 ml of the above solvent mixture, the mixture is stirred strongly for a night while about 1 g of the substance goes into solution. The solution is filtered and then applied onto the column. The colunn is eluted with the mentioned solvent mixture.

The pure fractions are evaporated while a suspension containing precipitate is obtained. The product is precipitated with acetone, filtered off, washed and finally dried. The purity of the product is examined by high pressure liquid chromatography. Decomposition temperature: 210°-214° C., $[\alpha]_D = -7.15°$ (c=0.42, water);

TLC: Silica gel 60 F 254 (DC-aluminium roll, art 5562, Merck), running agent: acetone and ammonium hydroxide in a ratio of 75:25—$R_f=0.5$; $R_t=9.81$ min (n-butanol:acetic acid:water=4:1:1).

Analysis for $C_{25}H_{31}O_9N_3$ (M=517.54) Calculated: C 58.02%; H 6.04%; N 8.12%. Found: C 58.30%; H 6.09%; N 8.03%.

EXAMPLE 10

3,6-Di-(β-D-glucopyranosyl-amino)-10-N-methyl-acridinium chloride 20.8 g (0.08 mole) of powdered 3,6-diamino-10-methyl-acridinium chloride and 35.2 g (0.16 mole+10%) of glucose-monohydrate are suspended in a mixture of 695 ml of acetone and 105 ml of distilled water. Under stirring the suspension is heated to 50° C. and then reacted with 5.6 ml of concentrated hydrochloric acid. The reaction mixture is stirred for another half an hour and then cooled to room temperature. The phases are separated from each other by decanting and the solid substance is washed twice by 650 ml of acetone. The product is dissolved in 250 ml of distilled water and the solution is dropped into 2500 ml of abs. ethanol under continuous stirring. 12.5 ml of a 10 percent sodium chloride solution are added to the opalescent solution. After some minutes a precipitate begins to separate. After two hours the precipitate is sucked off and suspended twice in 50 ml of ethanolfree water each, filtered off and washed with 150 ml of ether.

The precipitate is dissolved in 270 ml of distilled water, the solution is added drop by drop to 2700 ml of dry ethanol and in order to promote the precipitate formation some common salt solution is added. The described reprecipitation is repeated twice. 24.2 g (51.35%) of product are obtained.

Point of decomposition: 250° C.; $[\alpha]_D = +504°$ (c=0.80, water);

TLC: Silica gel 60 F254 (DC-aluminium roll, art. 5562, Merck), running agent: n-butanol, acetic acid and water in a ratio of 2:1:1—$R_f$=0.20.

Analysis for $C_{26}H_{34}O_{10}N_3Cl$ (M=583.76): Calcuated: C 53.49%; H 5.87%; N 7.20%. Found: C 53.12%; H 6.01%; N 7.32%.

FIG. 1 shows the carbon spectrum ($^{13}$C-NMR) of the starting substance 3,6-diamino-10-methyl-acridinium-chloride, FIG. 2 the same spectrum of the final product substituted by glucose in positions 3 and 6 at the amino group. The chemical shift of the carbon atoms of the sugar part is a proof for the pyranose structure of the glycoside while the coupling constants $^1J_{C1-H1}$ support the given anomer configuration. (The spectra were taken in DMSO-d$_6$.)

EXAMPLE 11

3,6-Di-($\beta$-D-galactopyranosyl-amino)-10-N-methyl-acridinium chloride 5.2 g of 3,6-diamino-10-methyl-acridine and 10.8 g of D-galactose are heated in 200 ml of a mixture of ethanol and water in a ratio of 88:12 under stirring until boiling. 1 ml of concentrated hydrochloric acid is added to the mixture, then it is boiled under reflux for an hour and stirred at room temperature for a day. Again 3.6 g of D-galactose are added and the mixture is boiled for another hour under reflux. The precipitate is separated and washed with a small amount of ethanol. Then the precipitate does not contain D-galactose any more, but 5–10% of the unreacted starting substance. The precipitate consists of mono- and digalactoside in a ratio of 1:4. Under slight heating the precipitate is dissolved in 60 ml of water and the solution is dropped into 700 ml of ethanol under stirring. The mixture is reacted with 2 ml of a 10 percent sodium chloride solution and then left to stand. The solid substance is filtered off, washed with some alcohol at first, then with ethylacetate and finally with ether, then it is dried in a vacuum desiccator. 7.4 g of product are obtained which contains unreacted starting substance practically no more and monoglycoside in a quantity of about 10–15%. The 4.9 g of substance obtained after three repeated reprecipitations contains still 5–10 g of monogalactoside as shown by the $^{13}$C-NMR-spectrum.

After five reprecipitations (yield 4.1 g=35%) no monoglycoside could be found in the product. Decomposition point: 200°–210° C.; $[\alpha]_D = +522.7°$ (c=0.90, water);

TCL: Silica gel 60 F 254 (DC-aluminium roll, art. 5562, Merck), running agent: butanol, acetic acid and water in a ratio of 2:1:1—$R_f$=0.14.

Analysis for $C_{26}H_{34}O_{10}N_3Cl$ (M=583.76): Calculated: C 53.49%; H 5.87%; N 7.20%. Found: C 53.05%; H 5.69%; N 7.29%.

EXAMPLE 12

3,6-Di-($\alpha$-L-rhamnopyranosyl-amino)-10-N-methyla-cridinium chloride

Under stirring 3.64 g (1.4×10$^{-2}$ mole) of 3,6-diamino-10-N-methyl-acridine are suspended in a mixture of 126 ml of acetone and 14 ml of water. The suspension is reacted with 0.7 ml of concentrated hydrochloric acid and boiled for two hours. Then 5.6 g (3.07×10$^{-2}$ mole) of L-rhamnose-monohydrate are added. The reaction mixture is boiled under reflux for six hours and then stirred at room temperature for a night. The precipitate is filtered off, washed on the filter at first with 10 ml of ethylacetate, then with 10 ml of ether and finally it is dissolved in 20 ml of water. 140 ml of acetone are added to the solution. The precipitate is separated and reprecipitated twice in the described manner.

The precipitate is now dissolved in 40 ml of warm water and then acetone is added (about 60 l) drop by drop until precipitation begins. This reprecipitation is repeated three times, too. The thus-obtained product consists of pure dirhamnoside. The amorphous solid substance is dissolved in 100 ml of water and the solution is lyophilized. Decomposition temperature: 250°–254° C.; $[\alpha]_D = +486.5°$; $[\alpha]_{578} = -52.2°$; $[\alpha]_{546} = -281.9°$ (water);

TLC: Silica gel 60 F 254 (DC-aluminium roll, art. 5562, Merck), running agent: n-butanol, acetic acid and water in a ratio of 3:1:1—$R_f$=0.16.

Analysis for $C_{26}H_{34}O_8N_3Cl$ (M=551.76): Calculated: C 56.70%; H 6.21%; N 7.65%. Found: C 56.65%; H 6.18%; N 7.49%.

EXAMPLE 13

3-Amino-6-($\alpha$-L-rhamnopyranosyl-amino)-10-methyl-acridinium chloride

The filtrates of the reprecipitations described in Example 12 are united and under stirring they are poured into 200 ml of acetone whereupon the monorhamnoside is separated. The substance is filtered off, dissolved in water and lyophilized.

Decomposition temperature: 216°–222° C.; $[\alpha]_D = -350.6°$; $[\alpha]_{578} = 363.6°$; $[\alpha]_{546} = -701.0°$ (water).

TLC: Silica gel 60 F 254 (DC-aluminium roll, art. 5562, Merck), running agent: n-butanol, acetic acid and water in a ratio of 3:1:1—$R_f$=0.42.

Analysis for $C_{20}H_{24}O_4N_3Cl$ (M=405.86): Calculated: C 59.19%; H 5.95%; N 10.35%. Found: C 59.85%; H 6.03%; N 10.41%.

EXAMPLE 14

3-Amino-6-($\beta$-lactosyl-amino)-10-N-methyl-acridinium chloride

A suspension of 2.60 g (10$^{-2}$ mole) of 3,6-diamino-10-N-methyl-acridine in 100 ml of a mixture of ethanol and water in a ratio of 7:3 is reacted with 0.2 ml of concentrated hydrochloric acid and then boiled until the solution becomes clear. After adding 5.40 g (1.5×10$^{-2}$ mole) of lactose-monohydrate the reaction mixture is stirred at boiling temperature for an hour and then at room temperature for a night. The separated precipitate is filtered off and under slight heating it is dissolved in 30 ml of water. The solution is dropped into 300 ml of ethanol under stirring. The reprecipitation is repeated. The precipitate is washed with 20 ml of ethylacetate, then with 20 ml of ether and dried in the open air. 2.03 g (34.8%) of a yellow, powdery substance are obtained. $[\alpha]_D = +226.1°$ (c=1.20, water);

TLC: Silica gel 60 F 254 (DC-aluminium roll, art. 5562, Merck), running agent: n-butanol, acetic acid and water in a ratio of 2:1:1—$R_f=0.32$.

Analysis for $C_{26}H_{34}N_{10}N_3Cl$ (M=584.02): Calculated: C 53.47%; H 5.87%; N 7.19%. Found: C 54.10%; H 5.91%; N 7.03%.

EXAMPLE 15

3,6-Di-(β-lactosyl-amino)-10-N-methyl-acridinium chloride 2.60 g ($10^{-2}$ mole) of 3,6-diamino-10-methyl-acridine are dissolved in 50 ml of water. 10.8 g ($3 \times 10^{-2}$ mole) of lactose-monohydrate and 0.2 ml of concentrated hydrochloric acid are added to the solution. The reaction mixture is stirred at 50° C. for 24 hours. At the 12th hour further 4 g ($1.11 \times 10^{-2}$ mole) of lactose-monohydrate and 0.2 ml of concentrated hydrochloric acid are added. After cooling the mixture is reacted with 200 ml of ethanol. An oily product separated which is isolated and dissolved in 100 ml of water. The solution is dropped into 600 ml of ethanol. By adding 200 ml of acetone the separation of the precipitate is promoted. The precipitate is washed with 20 ml of ethylacetate and then with 20 ml of ether and dried in the open air. 3.38 g of a yellow powder are obtained which is a mixture of equal parts of mono- and dilactosides.

The 10 percent solution of this mixture containing the dilactoside is dropped into the tenfold quantity of ethanol. By adding 2-3 drops of saturated sodium chloride solution the filtrability of the precipitate is improved. The repreciptation is repeted five times. The obtained dilactoside is chromatographically uniform. $[\alpha]_D = +253.9°$ (c=0.92, water);

TLC: Silica gel 60 F 254 (DC-aluminium roll, art. 5562, Merck), running agent: isobutanol, acetic acid and water in a ratio of 2:1:1—$R_f=0.12$.

Analysis for $C_{38}H_{54}O_{20}N_3Cl$ (M=907.92): Calculated: C 50.27%; H 6.00%; N 4.62%. Found: C 50.46%; H 6.08%; N 4.56%.

EXAMPLE 16

3,6-Di-(α,β-D-ribopyranosyl-amino)-10-methyl-acridinium chloride 2.60 g of 3,6-diamino-10-methyl-acridine and 4.50 g of D-ribose are stirred in a mixture of 90 ml of acetone and 10 ml of water at 40° C. for an hour after 0.2 ml of concentrated hydrochloric acid has been added. In the reaction the substances do not completely go into solution, but the character of the precipitate changes after a certain time. The precipitate gathers at the bottom of the flask. The solution is poured off, the precipitate is washed with some acetone and decanted again. Then the precipitate is dissolved in 50 ml of water and under stirring the solution is dropped into 200 ml of ethanol. After the addition of 600 ml of acetone it is left standing for a time, then the precipitate is filtered off and washed on the filter with some ethylacetate and some ether and dried in vacuo. 3.9 g of product are obtained which consists of—as it is provided by its thin layer chromatogram—about 30% of unreacted starting substance as well as of a mixture of mono- and diriboside in a ratio of 2:1 to 3:1. 1.4 g (13%) of pure diriboside are obtained by repreciptation seven times.

Decomposition temperature: 186°-200° C., $[\alpha]_D = +188.9°$ (c=0.24, water);

TLC: Silica gel 60 F 254 (DC-aluminium roll, art. 5562, Merck), running agent: methylethylketone, pyridine, water and acetic acid in a ratio of 70:15:15:5—$R_f=0.14$.

Analysis for $C_{24}H_{30}O_8N_3Cl$ (M=523.73): Calculated: C 55.04%; H 5.77%; N 8.02%. Found: C 55.21%; H 5.81%; N 7.91%.

By reacting the corresponding sugars in the manner described in Examples 1-16 the mono- and diglycosides, respectively, of the following ocompounds are obtained:

9-aminoacridine, 3-aminoacridine, 3,9-diaminoacridine, 4,9-diaminoacridine, 3,7-diaminoacridine, 9-amino-4-methylacridine, 9-amino-1-methylacridine, 9-amino-3-methylacridine, 9-amino-3-chloroacridine, 9-amino-2-chloroacridine, 9-amino-1-chloroacridine, 9-amino-5-chloroacridine, 3-amino-6-chloroacridine, 3-amino-7-chloroacridine, 1,6-diaminoacridine, 2,6-diaminoacridine, 1,9-diaminoacridine, 2,9-diaminoacridine, 9-amino-2,4-dimethylacridine, 9-amino-4,5-dimethylacridine, 9-amino-4-ethylacridine, 9-amino-1-methoxyacridine, 9-amino-4-methoxyacridine, 9-amino-1-chloroacridine, 9-amino-2-chloroacridine, 9-amino-3-chloroacridine, 9-amino-4-chloroacridine, 9-amino-1-nitroacridine, 9-amino-2-phenylacridine, 9-amino-2-carbomethoxyacridine, 9-amino-2-carbamoylacridine, 3-dimethyl-aminoacridine.

We claim:

1. A compound of the formula (I)

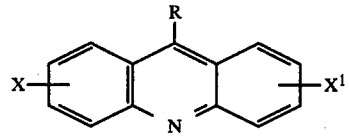

or a pharmaceutically acceptable salt thereof of the formula

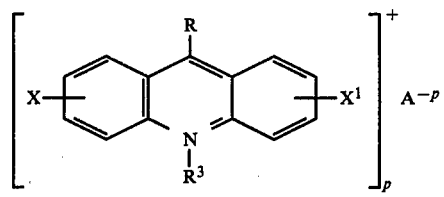

wherein R is hydrogen, a group of the formula (II)

wherein $R^1$ is hydrogen or methyl and $R^2$ is hydrogen or a sugar residue or R is dimethylamino;

X and $X^1$ are identical or different and are hydrogen, $-NR^1R^2$, dimethylamino, halogen, $C_1$ to $C_4$ alkoxy, nitro, cyano, carbomethoxy, carbamoyl, phenyl, or $C_1$ to $C_4$ alkyl-phenyl;

$R^3$ is hydrogen or $C_1$ to $C_5$ alkyl;

p is 1 or 2; and $A^{-p}$ is a pharmaceutically acceptable anion, with the restriction that at least one of the substituents R, X and $X^1$ represents a group of the formula $-NR^1R^2$ wherein $R^2$ is a sugar residue.

2. The compound or pharmaceutically acceptable salt thereof defined in claim 1 wherein the sugar residue is selected from the group consisting of D-glucosyl, D-galactosyl, D-mannosyl, D-xylosyl, D-arabinosyl, L-arabinosyl, D-ribosyl, 6-desoxy-D-glucosyl, 6-desoxy-D-galactosyl, L-rhamnosyl, 2-desoxy-D-arabinosyl, 2-acetamido-2-desoxy-D-galactosyl, 2-acetamido-2-desoxy-D-glucosyl, daunosaminyl, maltosyl, cellobiosyl, lactosyl, gentibiosyl, and laminarbiosyl.

3. 3,6-Di-($\beta$-D-Glucopyranosyl-amino)-acridine defined in claim 1.

4. 3-Amino-6-$\beta$-D-glucopyranosyl-amino-acridine defined in claim 1.

5. 3,6-Di-($\beta$-D-galactopyranosyl-amino)-acridine defined in claim 1.

6. 3,6-Di-(2', 3', 4', 6'-Tetra-O-acetyl-$\alpha$-D-galactopyranosyl-amino)-acridine defined in claim 1.

7. 3,6-Di-(2', 3', 4', 6'-Tetra-O-acetyl-$\alpha$-D-galactopyranosyl-amino)-acridine defined in claim 1.

8. 3,6-Di-($\alpha$-L-Rhamnopyranosyl-amino)-acridine defined in claim 1.

9. 3,6-Di-($\alpha$-D-Ribopyranosyl-amino)-acridine defined in claim 1.

10. 3,6-Di-($\beta$-Lactopyranosyl-amino)-acridine defined in claim 1.

11. 3-($\beta$-D-Glucopyranosyl-amino)-6-($\alpha$-L-rhamnopyranosyl-amino)-acridine defined in claim 1.

12. 3,6-Di-($\alpha$-D-glucopyranosyl-amino)-10-methyl-acridiniumchloride defined in claim 1.

13. 3,6-Di-($\beta$-D-galactopyranosyl-amino)-10-N-methyl-acridinium chloride defined in claim 1.

14. 3,6-Di-($\alpha$-L-Rhamnopyranosyl-amino)-10-N-methyl-acridinium chloride defined in claim 1.

15. 3-Amino-6-($\alpha$-L-rhamnopyranosyl-amino)-10-methyl-acridinium chloride defined in claim 1.

16. 3-Amino-6-($\beta$-lactosyl-amino)-10-N-methyl-acridinium chloride defined in claim 1.

17. 3,6-Di-($\beta$-Lactosyl-amino)-10-N-methyl-acridinium chloride defined in claim 1.

18. 3,6-Di-($\alpha,\beta$-D-Ribopyranosyl-amino)-10-methyl-acridinium chloride defined in claim 1.

19. A process for the preparation of a compound of the formula (I)

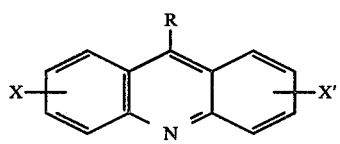

or a pharmaceutically acceptable salt thereof of the formula

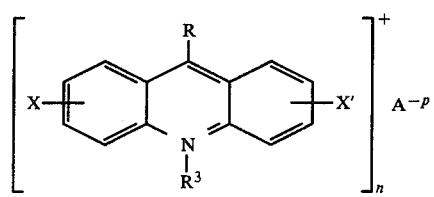

wherein R is hydrogen, a group of the formula (II)

wherein
  $R^1$ is hydrogen or methyl and
  $R^2$ is hydrogen or a sugar residue, or R is dimethylamino,
  X and $X^1$ are identical or different and are hydrogen, —$NR^1R^2$, dimethylamino, halogen, $C_1$ to $C_4$ alkyl, $C_1$ to $C_4$ alkoxy, nitro,
  cyano, carbomethoxy, carbamoyl, phenyl, or $C_1$ to $C_4$ alkyl-phenyl; p is 1 or 2; and
  $A^{-p}$ is a pharmaceutically acceptable anion, with the restriction that at least one of the substituents R, X and $X^1$ represent a group of the formula —$NR^1R^2$ wherein $R^2$ is a sugar residue, which comprises the step of:

reacting a compound of the formula (III)

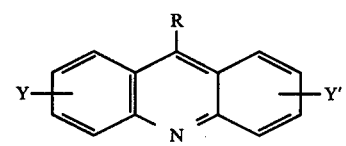

or a pharmaceutically acceptable salt thereof of the formula

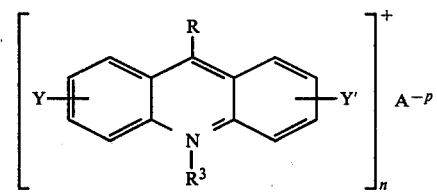

wherein
  Y and $Y^1$ are identical or different and stand for hydrogen, an amino, methylamino, halogen, $C_1$ to $C_4$ alkyl, $C_1$ to $C_4$ alkoxy, nitro, cyano, carbomethoxy, carbamoyl, phenyl or $C_1$ to $C_4$ alkyl-phenyl, in a polar solvent containing water in the presence of an acid catalyst with a sugar selected from the group consisting of D-glucose, D-galactose, D-mannose, D-xylose, D-arabinose, L-arabinose, D-ribose, 6-desoxy-D-galactose, L-rhamnose, 2-desoxy-D-arabinose, 2-acetamido-2-sesoxy-D-glucose, daumosamine, maltose, cellobiose, lactose, gentibiose, and laminarbiose, to yield the desired product.

20. The process defined in claim 19 wherein the polar solvent is an alcohol or a ketone.

21. The process defined in claim 19 wherein the reaction is catalyzed by hydrochloric acid.

22. The process defined in claim 19 wherein the reaction medium contains 7 to 20% water.

23. The process defined in claim 19 wherein the reaction is carried out at 20°–95° C.

24. An antimicrobial pharmaceutical composition which comprises an antimicrobially effective amount of a compound of the formula I as defined in claim 25 or an antimicrobially effective amount of a pharmaceutically acceptable salt thereof in combination with an inert carrier.

25. A method of treatment for a subject having a microbial disease which comprises the step of administering to said subject an antimicrobially effective amount of the compound defined in claim 1 or an antimicrobially effective amount of a pharmaceutically acceptable salt thereof.

* * * * *